United States Patent [19]

Motta

[11] 4,237,287

[45] Dec. 2, 1980

[54] PROCESS FOR OBTAINING 4,5-DICHLORO-2-PHENYL-3(2H)-PYRIDAZINONE FROM 5-CHLORO-4-AMINO-2-PHENYL-3(2H)-PYRIDAZINONE

[75] Inventor: Raimondo Motta, Milan, Italy

[73] Assignee: Oxon Italia S.p.A., Milan, Italy

[21] Appl. No.: 56,399

[22] Filed: Jul. 10, 1979

[30] Foreign Application Priority Data

Jul. 28, 1978 [IT] Italy ............................. 83624 A/78

[51] Int. Cl.³ ................ C07D 237/14; C07D 237/22; C07D 498/04
[52] U.S. Cl. .................................. 544/241; 544/236; 544/240
[58] Field of Search ................... 544/241, 236, 240

[56] References Cited
PUBLICATIONS

Peters et al., J. Chem. Soc. 1943, 233.

*Primary Examiner*—Mark L. Berch
*Attorney, Agent, or Firm*—Young & Thompson

[57] ABSTRACT

In a process for obtaining 4,5-dichloro-2-phenyl-3(2H)-pyridazinone from 5-chloro-4-amino-2-phenyl-3(2H)-pyridazinone the 5-chloro-4-amino-2-phenyl-3(2H)-pyridazinone is diazotized in a first stage in accordance with the following reaction:

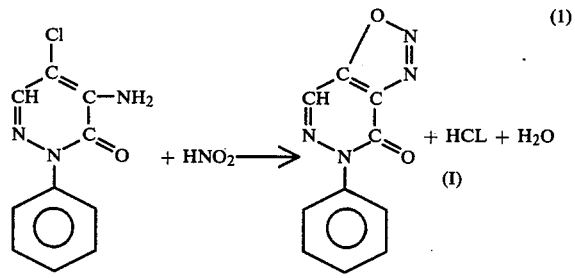

the compound (I) being obtained by dilution with water and filtration. In a second stage of the process the compound (I) is reacted with thionyl chloride in accordance with the following reaction:

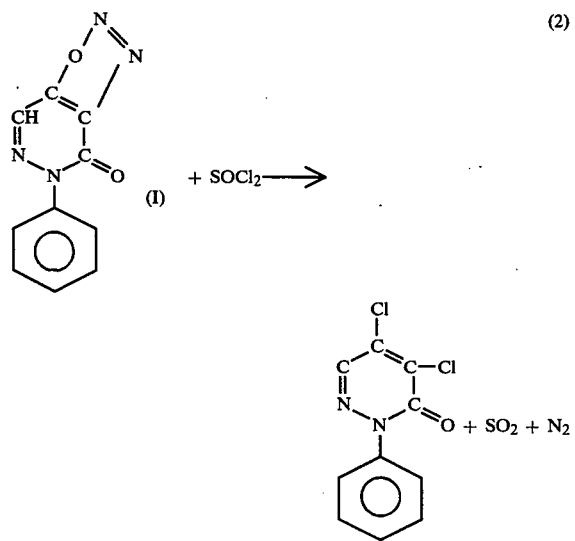

the 4,5-dichloro-2-phenyl-3(2H)-pyridazinone being obtained by dilution with water and filtration.

3 Claims, No Drawings

PROCESS FOR OBTAINING 4,5-DICHLORO-2-PHENYL-3(2H)-PYRIDAZINONE FROM 5-CHLORO-4-AMINO-2-PHENYL-3(2H)-PYRIDAZINONE

BACKGROUND OF THE INVENTION

It is well-known in the art that amination of 4,5-dichloro-2-phenyl-3(2H)-pyridazinone (PCC) leads to the formation of so-called commercial Pyrazon, that is a mixture of two isomers, one of which, 5-amino-4-chloro-2-phenyl-3(2H)-pyridazinone (PCA) is active as a selective weed-killer or herbicide, while the second, 4-amino-5-chloro-2-phenyl-3(2H)-pyridazinone (ISO-PCA), is inactive as a weed-killer.

SUMMARY OF THE INVENTION

The object of the present invention is to transform the 4-amino-5-chloro-2-phenyl-3(2H)-pyridazinone (ISO-PCA) into 4,5-dichloro-2-phenyl-3(2H)-pyridazinone (that is, into the starting product for the synthesis of commercial Pyrazon by means of amination). By such a transformation, the mixture of the two isomers PCA and ISO-PCA is again obtained and this is ultimately equivalent to transforming the isomer which is inactive as a weed-killer into the active isomer, inasmuch as it is also possible and already known to separate the two isomers which make up commercial Pyrazon.

The process to which the present invention relates is characterized by the fact that it is performed in accordance with the following two reactions:

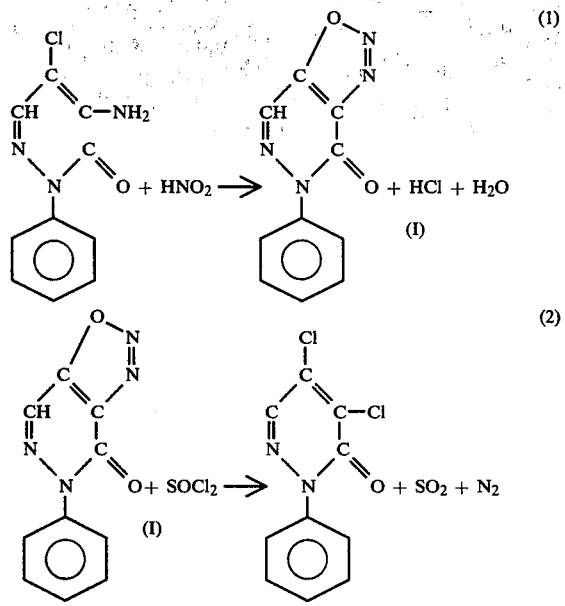

which are not known from the literature.

DESCRIPTION OF THE PREFERRED EMBODIMENT

In substance, 5-chloro-4-amino-2-phenyl-3(2H)-pyridazinone is first reacted with sodium nitrite in concentrated HCl and at low temperature in conditions such as to bring the ISO-PCA into solution completely, subsequent dilution with water and filtration being then provided to obtain a solid chemical product, not known in the art or in the literature, which unexpectedly derives from the diazotization of the amino group of the starting compound and from subsequent elimination of HCl with closing of the ring.

In a second stage, the unknown chemical compound obtained in the first, the structure of which is confirmed by various types of analyses and the characteristics of which have been identified, is reacted, suitably dried, with thionyl chloride in dimethylformamide, the 4,5-dichloro-2-phenyl-3(2H)-pyridazinone being then separated by dilution with water and subsequent filtration.

As already stated, it is already known to obtain commercial Pyrazon, that is a mixture of PCA with ISO-PCA, from the compound produced, so that the object of the invention can be said to have been achieved.

The Example appearing hereinafter is given purely by way of illustration of the invention and naturally does not have any limitative character.

EXAMPLE

In a reaction vessel there are placed, for the first stage:

1000 ml of 37% HCl
and then
111 g of ISO-PCA

Dissolution is complete.

Diazotization is carried out between −10° C. and 0° C. by adding drop by drop a solution of 38 g of $NaNO_2$ in 250 ml of water.

At the end of the addition, conditioning takes place for half an hour. Dilution is carried out with 100 ml of water, cooling being effected. After conditioning, the precipitate is filtered off, washed to neutrality with water and dried.

93 g of an unknown solid product having the formula I on the right of reaction (1) appearing above are obtained with a yield of 87% of the theoretical, the melting point of the product being about 113°–114° C.

For the second stage of the process, the following are then placed in a reaction vessel:

750 ml of dimethylformamide
100 ml of thionyl chloride
50 g of the said compound (I).

The mixture is heated to 70°–75° C. and is held at 70°–75° C. for 1½ hours.

Cooling and dilution with 750 ml of water are carried out. The product is filtered off, washed to neutrality and dried. 52 g of 4,5-dichloro-2-phenyl-3(2H)-pyridazinone are obtained, giving a yield of 92.4% of the theoretical.

The product (PCC) obtained has a melting point of 164°–165° C. and centesimal analysis thereof provides the following data:

| C theor. | H | N | Cl |
|---|---|---|---|
| 49.8% (49.79) | 2.45% (2.48) | 11.55% (11.61) | 29.23% (29.46) |
| O | | | |
| 6.97% (6.64) | | | |

From the PCC produced in this way it is possible to obtain commercial Pyrazon again by means of amination, so that the object of the invention can be considered to have been achieved. In fact, it is known from U.S. application Ser. No. 49,654, filed June 18, 1979, of the same Applicants to separate commercial Pyrazon into its two component isomers PCA and ISO-PCA, so that it will be possible without particular problems to obtain all the product in the form of PCA, that is as active compound from the herbicidal point of view. This will entail the double advantage of being able, on the one hand, to distribute the active compound alone over the soil for weed-killing treatments, eliminating all unnecessary and harmful pollution, and, on the other hand, to transform all the product into active substance without having any waste or discarding of material.

I claim:

1. Process for obtaining 4,5-dichloro-2-phenyl-3(2H)-pyridazinone from 5-chloro-4-amino-2-phenyl-3(2H)-pyridazinone, characterized in that the 5-chloro-4-amino-2-phenyl-3(2H)-pyridazinone is diazotized in a first stage in accordance with the following reaction:

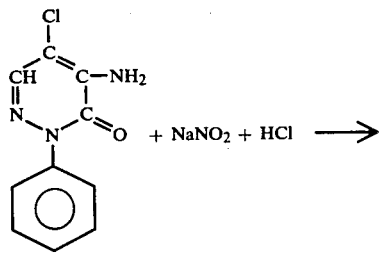

(1)

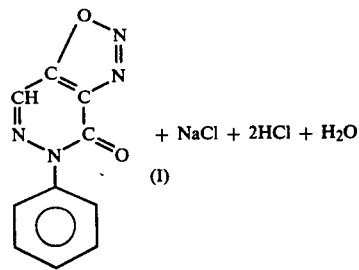

the compound (I) being obtained by dilution with water and filtration, and in that in a second stage the said compound (I) is reacted with thionyl chloride in accordance with the following reaction:

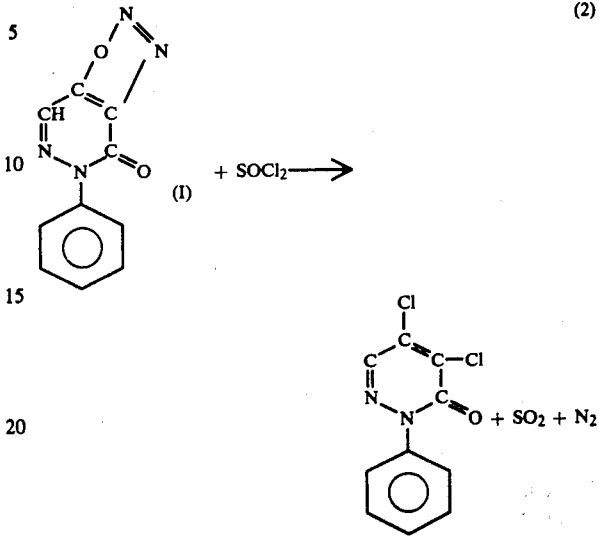

the 4,5-dichloro-2-phenyl-3(2H)-pyridazinone being obtained by dilution with water and filtration.

2. Process as claimed in claim 1, wherein the first stage of diazotization is carried out in solution with concentrated hydrochloric acid with sodium nitrite at a temperature between −20° C. and +5° C., while the reaction of the second stage is carried out in dimethylformamide at a temperature between 40° and 100° C.

3. Process as claimed in claim 2, wherein the temperature of the reaction of the first stage is between −10° and 0° C. and that of the reaction of the second stage is between 70° and 75° C.

* * * * *